United States Patent
Krause et al.

(10) Patent No.: US 6,338,714 B1
(45) Date of Patent: Jan. 15, 2002

(54) MEDICAL TREATMENT AND SUPPLY CENTER

(75) Inventors: Hartmut Krause, Erlangen; Peter Noegel, Effeltrich; Roland Betz, Viereth-Trunstadt, all of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/550,223

(22) Filed: Apr. 14, 2000

(30) Foreign Application Priority Data

Apr. 15, 1999 (DE) .......................................... 199 17 089

(51) Int. Cl.[7] ................................................. A61B 5/00
(52) U.S. Cl. ....................................... 600/300; 128/897
(58) Field of Search ................................. 600/300–301; 221/1, 210–211; 406/1, 198; 705/2–3; 128/898, 897

(56) References Cited

U.S. PATENT DOCUMENTS

| 5,133,338 A | | 7/1992 | Wess et al. | |
| 5,427,743 A | * | 6/1995 | Markin | ........................ 422/104 |
| 6,048,086 A | * | 4/2000 | Valerino, Sr. | ................... 705/2 |

* cited by examiner

Primary Examiner—Robert L. Nasser
Assistant Examiner—Michael Astorino
(74) Attorney, Agent, or Firm—Schiff Hardin & Waite

(57) ABSTRACT

A medical treatment and supply center with a treatment location has a number of medical devices and systems, with at least some of the medical devices and systems as well as their assemblies, subsystems and components are arranged in a central magazine and can be transferred therefrom to the desired treatment location by at least one automatic conveyor.

4 Claims, 2 Drawing Sheets

MEDICAL TREATMENT AND SUPPLY CENTER

BACKGROUND OF THE INVENTION

1. Field of the Invention

The present invention is directed to a medical treatment and supply center having one or more treatment rooms with a number of medical devices and systems.

2. Description of the Prior Art

The equipping of medical treatment and supply centers entails a number of system-dependent disadvantages that not only make work more difficult but also can produce hazards for the patient in individual cases. Often the correct device is present for the current application, but with an inadequate component. For example, a 7 inch image intensifier is needed for surgery but the x-ray system that is present has a 9 inch image intensifier permanently installed. Due to the multitude of devices utilized in alternation, the treatment and diagnosis rooms are often overfilled and disorderly, so that work with the respectively necessary device is impeded by the devices not required at the moment. Given a device outage in a treatment room, moreover, a replacement often cannot be acquired or cannot be acquired fast enough, since no one in the treatment room knows where a backup device may be and how it could be brought rapidly to a use position, etc.

European Application 0 288 698 discloses a medical treatment and supply center with a device arrangement that includes a locating/diagnosis apparatus and a therapy apparatus. The locating/diagnosis apparatus and the therapy apparatus are arranged spatially separated from one another around a base disposed in the spatial center of the workstation, and provided with a patient support such that the various medical devices can be reached by swivel motions of the patient support around the base. The patient borne on the patient support no longer has to be transferred from one bed to another for various medical measures to be undertaken at the patient due to the arrangement of the medical devices around the patient support table; rather, the patient supported on the patient support table can be pivoted to the desired medical device in a simple way. An ordered workstation is achieved due to the systematic arrangement of the medical devices. Measures for offering backup devices given a device outage or measures for equipping the medical devices with components suitable for the respective application, however, are not undertaken at the workstation.

SUMMARY OF THE INVENTION

An object of the present invention is to provide a medical treatment and supply center of the type initially described wherein an optimum equipping of the treatment center is possible with fewer devices and supporting apparatus dependent on the currently occurring treatment or diagnosis.

This object is achieved in a medical treatment and supply center in accordance with the invention wherein at least some of the medical devices and systems as well as their assemblies, subsystems and components are arranged in a central magazine and can be transferred therefrom to the desired treatment location by at least one automatic conveyor that can be equipped with these devices and systems as well as their assemblies, subsystems and components. The conveyor means is preferably fashioned such that it can upgrade, dismantle and re-equip the medical devices and systems at the treatment location on the basis of automatic attachment of assemblies, subsystems and components as needed.

All possible devices at every treatment location and in every treatment room are not made available by the inventive embodiment; rather, the selection ensues in an application-specific manner for the respective application. This can ensue especially simply in conjunction with the prior reservation of the treatment and diagnosis rooms. As is known, of course, operating rooms or the like must be reserved an adequately long time in advance for the pending treatments.

In an embodiment of the invention, a central control unit contains the device and system requirements for all important diagnoses and treatments in sub-programs, and the necessary equipment is taken from the magazine and configured automatically via the central acquisition of the respective equipping of the treatment rooms and in conformity with the advance reservation of a room.

In a further embodiment of the invention, the conveyor can be a robot arm controlled by a central control unit for the automatic pick-up and manipulation of all devices and assemblies. The robot arm can be arranged at a freely movable mobile mount, preferably a motor-driven transport carriage that is guided at rails on the floor or suspended from the ceiling.

DESCRIPTION OF THE PREFERRED EMBODIMENTS

Figure 1:
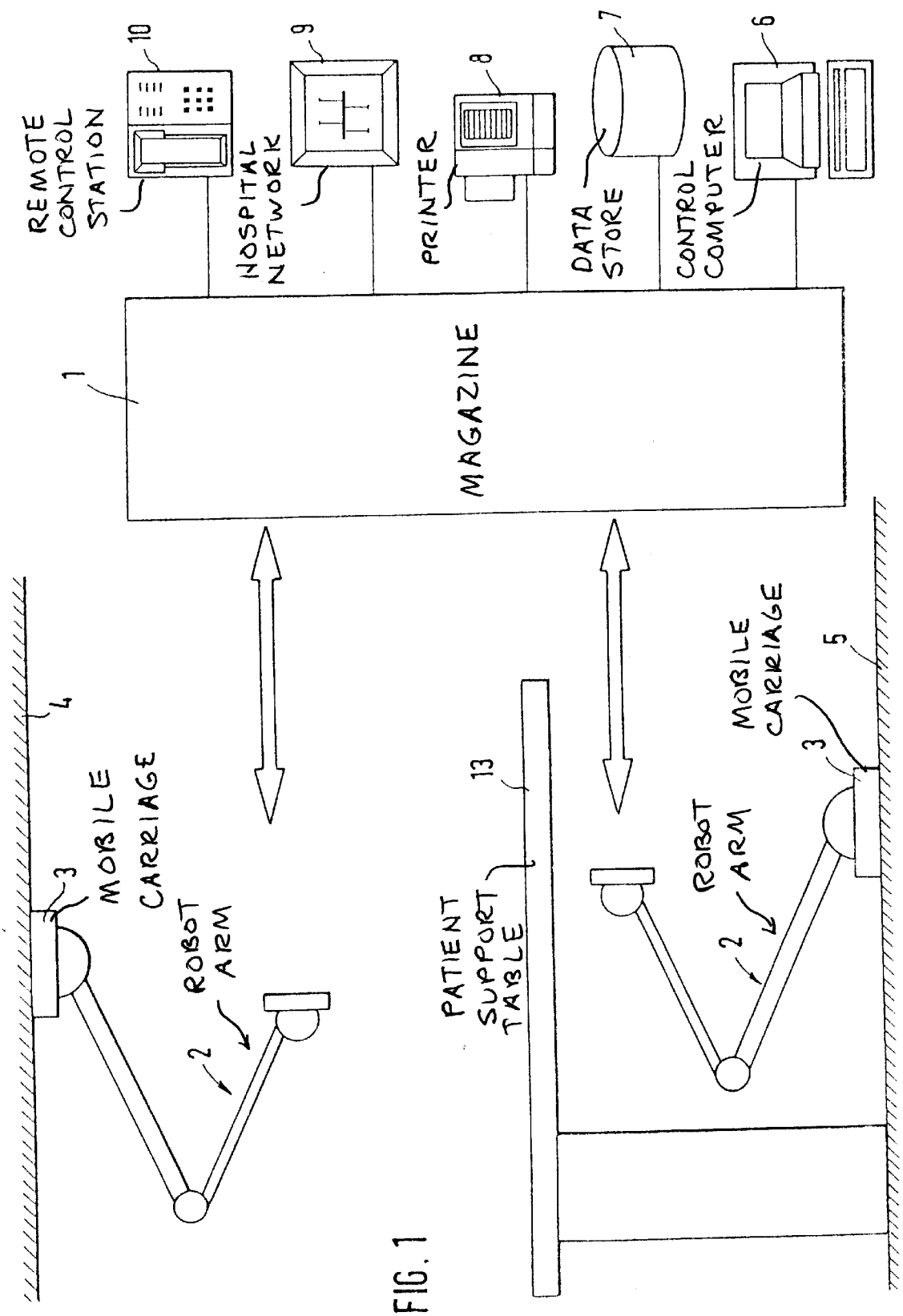
FIG. 1 is a block diagram of a magazine system in accordance with the invention.
Figure 2:
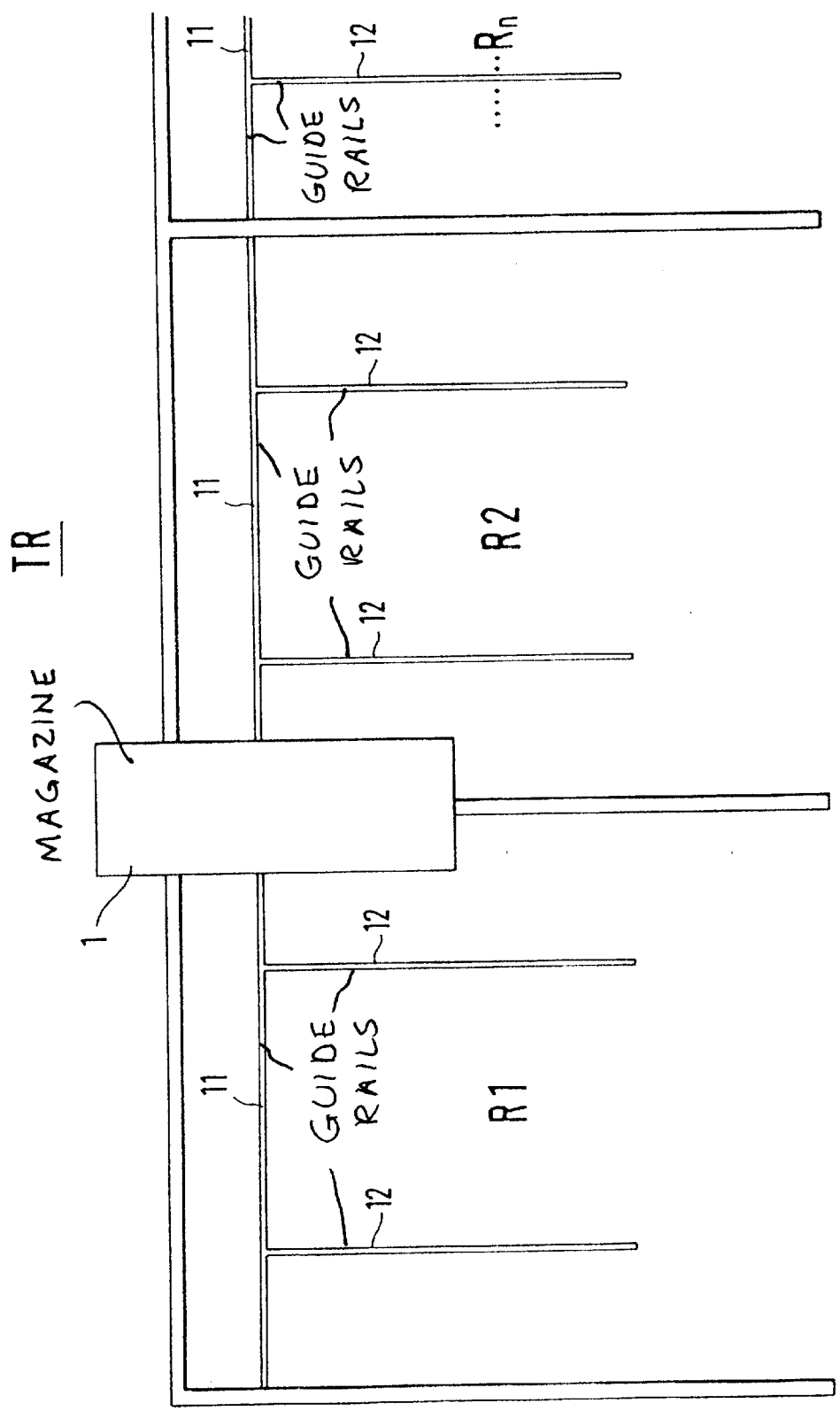
FIG. 2 shows a schematic floor plan of a medical treatment and supply center having a central device magazine in accordance with the invention.

FIG. 1 shows a medical treatment and supply center having a magazine 1 that, in the exemplary embodiment shown in FIG. 1, is arranged in a treatment room. As shown in FIG. 2, however, the magazine 1 alternatively can be arranged in a treatment and supply center having a number of treatment rooms. For the diagnosis and treatment of patients (not shown) the magazine 1 contains the necessary medical devices and systems as well as their subsystems, components and assemblies such as, for example, x-ray tubes, image intensifiers, endoscopy units, ultrasound units, ultrasound probes, shockwave heads and incidental components as well. An automatic conveyor is provided in the form of a robot arm 2 fashioned as a manipulation and support arm in the exemplary embodiment. In the exemplary embodiment of FIG. 1, the robot arm can be moved as desired with the assistance of a motor-driven carriage 3 at rails below the ceiling 4 or on the floor 5. The robot can be controlled via a central control unit so that it automatically takes the medical systems and devices as well as their assemblies, subsystems and components needed in a specific treatment room from the magazine 1 and places them at the respective treatment location, for example in the proximity of the patient support table 13, or automatically attaches them to the devices present thereat. To this end, a connection of the hospital network 9 to the magazine 1, for example via a bus line, can be provided in addition to a control computer 6 as central control unit, a data store 7 and a printer 8, as can the coupling of the magazine 1 to a remote control station 10.

Dependent on the type of treatment or diagnosis, the devices and systems as well as their assemblies, subsystems and components are taken from the magazine 1 with one or more robot arms 2 and, if necessary, are positioned relative to one another with the required precision, for example, the x-ray tube relative to the image intensifier unit and the shockwave head therefor in a lithotripsy application. A number of components of different power and configuration can be stored for one type of component. Optimally, each robot arm 2 should be fashioned such that it can carry and install every occurring component. The robot arms 2 also have a standby position, so that they can be re-equipped even during treatment. The central control computer 6 enables a pre-setting of a specific sequence. Obviously, a number of treatment or diagnosis rooms can be serviced with one magazine 1, in which case it is expedient when the robot arms 2 and the devices, systems, assemblies, subsystems and components have a shared mechanical, electrical and EDP interface available to them, so that the devices, systems, subsystems and components can be automatically recognized and properly operated.

FIG. 2 schematically indicates how a number of treatment rooms $R_1$ through $R_n$ can be supplied with the necessary medical devices and systems as well as their assemblies, subsystems and components with the assistance of a central magazine 1. Guide rails 11 and 12 at the floor are schematically indicated, the transport carriage 3 with the robot arms being able to be brought to any desired position of every room with the carriage 3 in order to deliver a specific device or a specific device group thereto, or to remove it and take into the magazine 1 and replace with a different device having the same or a different specification.

There is also the possibility of storing sub-programs in the data store 7 that contain the device and system requirements for different diagnoses and treatments and of implementing these as needed with the central control computer 6. Since the control computer, as a central control unit, knows the respective equipping of the treatment rooms $R_1$ through $R_n$ on the basis of the standard prior reservations of the treatment rooms $R_1$ through $R_{n,which\ are}$ required these, it can drive the robot arm 2 such that it takes only the equipment of a treatment room required for the respective diagnosis or treatment from then magazine 1 and correspondingly orients them at the treatment location.

Access to the individual treatment rooms $R_1$ through $R_n$ takes place at the bottom in FIG. 2, and a technical room is expediently provided thereabove at which re-equipping of the magazine 1 can take place and where potentially malfunctioning devices or assemblies can be repaired as needed.

If the correct device was in fact present for a current application but with an inadequate component, for example a seven inch image intensifier for surgery but the x-ray system has a 9 inch image intensifier permanently installed, then the suitable component can always be fetched from the magazine 1 by one of the robot arms 2 as a result of the inventive magazine system in conjunction with the robot arms 2 and can be operated at the basic system. Only the currently required units are respectively in the treatment room, this thus not being overfilled and, thus, difficult to use. After being used, the units are again made available to other rooms. As a result thereof, the usage and the availability of the individual systems are enhanced. When a specific medical system goes down in a treatment room due to a fault, a backup system was hitherto fetched, with the result that people stood around more, service was informed and a technician must come to the diagnosis and treatment room for the repair, this room being thereby blocked. As a result of the inventive fashioning of the medical treatment and supply center, a backup system is fetched from the magazine 1 for the current operation, whereby a component that may initially be somewhat poorer is also selected under certain circumstances when the device that is down is not available in the respective, high-quality specification. The magazine system informs service personnel and makes the malfunctioning component available for repair in a free room or in the aforementioned, specific technology room. The use of the respective treatment room is thus not impeded by the repair of a malfunctioning device.

Another example of how the number of device parts to be kept on hand can be reduced by the invention is that case wherein the hospital, for example, has a lithotripter (ESWL system) available to it. Pain therapy (ESWT) has been found to be a type of treatment and has been established as a method by medical research. The hospital must now additionally acquire a ESWT system that differs from the lithotripter mainly on the basis of the significantly lower energy flux density. When the hospital is equipped with an inventive medical treatment and supply center, the hospital only purchases a further shockwave head with lower power and a software expansion for its magazine, so that lower-energy pressure pulses can then be applied by simply replacing this shockwave head.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical treatment and supply center comprising:
    a treatment location;
    a plurality of medical devices and systems and associated assemblies, sub-systems and components, for use in selected combinations for administering treatment at said treatment location;
    a conveyor apparatus, equipped with some of said medical devices and systems, as equipped medical devices and systems, and with assemblies, sub-systems and components associated with said equipped medical devices and systems, said conveyor apparatus being movable for transferring said equipped medical devices and systems and the associated assemblies, sub-systems and components to said treatment location automatically; and
    said conveyor apparatus also automatically upgrading, dismantling and re-equipping said equipped medical devices and systems at said treatment location by automatically attaching selected associated assemblies, sub-systems and components to said equipped medical devices at said treatment location.

2. A medical treatment and supply center as claimed in claim 1 wherein said conveyor apparatus comprises a robot arm, and a central control unit operating said robot arm, for automatically picking up and manipulating said medical devices and systems and said assemblies, sub-systems and components.

3. A medical treatment and supply center as claimed in claim 2 further comprising a plurality of guide rails, along which said robot arm is movable, arranged for guiding said robot arm to and from said treatment location.

4. A medical treatment and supply center as claimed in claim 3 wherein said treatment room comprises one of a plurality of treatment rooms, and wherein said central control unit automatically controls said robot arm to select said equipped components, and the associated assemblies, sub-systems and components, at a central equipping location and controls movement of said robot arm from said central equipping location to a selected one of said treatment rooms dependent on a prior designation of a treatment to be administered in said one of said treatment rooms entered into said central control unit.

* * * * *